United States Patent
Lindhofer et al.

(10) Patent No.: US 6,294,167 B1
(45) Date of Patent: Sep. 25, 2001

(54) PHARMACEUTICAL COMPOSITIONS FOR IMMUNOTHERAPY CONTAINING ANTIBODIES WHICH SPECIFICALLY RECOGNIZE THE MHCII ANTIGEN OF A PATIENT TO BE TREATED

(75) Inventors: Horst Lindhofer, Gröbenzell; Stefan Thierfelder, Eichenau, both of (DE)

(73) Assignee: GSF-Forschungszentrum fur Umwelt und Gesundheit GmbH, Oberschleissheim (DE)

( * ) Notice: Subject to any disclaimer, the term of this patent is extended or adjusted under 35 U.S.C. 154(b) by 0 days.

(21) Appl. No.: 09/029,369

(22) PCT Filed: Aug. 23, 1996

(86) PCT No.: PCT/EP96/03733

§ 371 Date: Nov. 23, 1998

§ 102(e) Date: Nov. 23, 1998

(87) PCT Pub. No.: WO97/07819

PCT Pub. Date: Mar. 6, 1997

(30) Foreign Application Priority Data

Aug. 25, 1995 (DE) .............................. 195 31 346

(51) Int. Cl.$^7$ .......................... A01N 63/00; A61K 39/395
(52) U.S. Cl. ................ 424/93.7; 424/93.71; 424/136.1; 424/137.1; 424/130.1
(58) Field of Search ................. 424/130.1, 93.7, 424/93.71, 136.1, 137.1

(56) References Cited

U.S. PATENT DOCUMENTS 4,676,980  6/1987  Segal et al. .

FOREIGN PATENT DOCUMENTS 1329545  5/1995  (CA) .
0 068 790 A2  1/1983  (EP) .

OTHER PUBLICATIONS

Garrido, F., et al., "Natural history of HLA expression during tumour development," Immunology Today 14(10):491–499 (1993).

Huang, Yi–Wu and Ellen S. Vitetta, "Immunotherapy of Multiple Myeloma," Stem Cells 13: 123–134 (1995).

Link, B.K., et al., "Humanized BsF(ab')2 Anti–CD3–Based Bispecific Monoclonal Antibody Designed for Therapy of B–Cells Malignancies," J. of Investigative Medicine 43(3): 482A (1995).

Seon, B.K., et al., "Four groups of new monoclonal antibodies which are directed to individually different cell surface antigens on human leukemia–lymphoma cells and whose conjugates with ricin a chain are effective for specific tumor cell killing," The FASEB Journal Abstract No. 6509 6(5):A2060 (1992).

Wu, Samuel, et al., "Use of Bispecific Heterconjugated Antibodies (Anti–T Cell Antigen Receptor x Anti–MHC Class II) To Study Activation of T–Cells with a Full Length of Truncated Antigen Receptor ζ–Chain," The Journal of Immunology 150(6):2211–2221 (1993).

Yagi, Junji, et al., "Superantigen–Like Properties of an Antibody Bispecific for MHC Class II Molecules and the $V_{62}$ Domain of the T Cell Antigen Receptor," J. of Immunology 152:3833 (1994).

*Primary Examiner*—Geetha P. Bansal
(74) *Attorney, Agent, or Firm*—Roylance, Abrams, Berdo & Goodman, L.L.P.

(57) ABSTRACT

The invention concerns medicaments containing antibodies which have at least one specificity and detect the MHCII antigen of a patient to be treated. The invention further concerns antibodies with two or more specificities which detect the MHCII antigen of a patient, and diagnostic compositions containing these antibodies.

13 Claims, 9 Drawing Sheets

PHARMACEUTICAL COMPOSITIONS FOR IMMUNOTHERAPY CONTAINING ANTIBODIES WHICH SPECIFICALLY RECOGNIZE THE MHCII ANTIGEN OF A PATIENT TO BE TREATED

Pharmaceutical compositions for immunotherapy containing antibodies which specifically recognize the MHCII-antigen of a patient to be treated The present invention relates to pharmaceutical compositions for immunotherapy, containing antibodies which specifically recognize the MHCII-antigen of a patient to be treated, or antibodies with one or more specificities which have at least one antigen-binding site which specifically recognizes the MHCII-antigen of a patient to be treated, and their use for preparing pharmaceutical compositions for immunotherapy. The herein described pharmaceutical compositions and antibodies are in particular suitable for immunotherapy after MHCII-incompatible bone marrow transplantation (KMT).

Bone marrow transplantation as such suggests itself as sufficient therapy for leukemic patients suffering from a recurrence of leukemia in spite of chemotherapy. Bone marrow transplantations permit long term remissions and curing, with the result that patients live 20 years and longer and can be considered to have been cured. However, many patients who have undergone bone marrow transplantation still die from leukemia recidivation, the metastatic spread of the original leukemia. Obviously, the reason therefor is that the irradiation of the whole body and the highly dosed chemotherapy which precede the transplantation of intact bone marrow to compensate for the patient's lost blood formation, are often insufficient to permanently eliminate the last malign leukemic cells. Within the last 14 years, no substantial progress in the reduction of the percentage of the patients with leukemia recidivation after bone marrow transplantation has been made. The therapeutical possibilities to date seem to be exhausted in this respect. New approaches to possible therapies to eliminate residual leukemic cells surviving chemotherapy and irradiation consider in particular a tumor-immunological cell therapy which should make use of antibodies recognizing cell markers which are specifically present on leukemic cells. A substantial, so far unsolved problem consists in the fact that it has not been possible to identify any tumor-specific marker antigens by which leukemic cells could be distinguished from non-malign blood cells (Kranz et al., Blood 73 (1989), 1942). Only B-cell tumors form individual-specific, idiotypical immunoglobulins which (relative to an individual patient) can be considered tumor-specific antigens. As investigations with chemically conjugated, bispecific antibodies have shown, these immunoglobulins on the cells tend to undergo modulation and mutation, thereby eluding recognition by antibodies specifically directed against them (Stevenson et al., Blood 77 (1991), 1071). Therefore, the knowledge existing to date is insufficient to eliminate leukemia cell clones by immunological cell therapy.

Hence, the present invention addresses the problem of providing antibodies and pharmaceutical compositions containing the same which allow particular target cells, in particular tumor cells, to be distinguished from other cells on account of the recognition of specific marker antigens, and which are therefore suitable for an immunological cell therapy.

This problem is solved by the provision of the embodiments characterised in the patent claims.

Thus, the present invention relates to pharmaceutical compositions containing antibodies having at least one specificity for the MHCII-antigen of the patient to be treated.

Such pharmaceutical compositions lend themselves to the in vivo and in vitro therapy of different tumor types and the suppression of host-versus-graft-reactions and autoimmune reactions and are suitable to generally elicit immunosuppression. They can, for instance, be used for immunological cell therapy in tumor recidivation after MHCII incompatible bone marrow transplantation, that is transplantation in which the donor's MHCII antigen differs from the receiver's. As described above, bone marrow transplantation is often resorted to as a last means to fight chemotherapy-resistant types of leukemia. Of these, especially B-cell lymphomas, but also other types of leukemia which derive from cells resulting from hematopoiesis frequently express the histocompatibility antigen MHCII. This surface antigen is highly polymorphous, and the different types can be recognized by specific antibodies. As all immunocompetent cells (from the donor) growing in the patient after an MHCII incompatible bone marrow transplantation possess an MHCII type different from that of the tumor, the tumor can be highly selectively identified and eliminated by antibodies recognizing the receiver's MHCII type. It is true that apart from the cells of the immunological system there are other types of cells which express MHCII-antigen, such as the liver cells, but the expression and antigen population on the cell surface is so low with these cell types compared to malign cells of the immunological system that a specific recognition of the tumor cells which express MHCII-antigen is ensured and other cells or tissues are not damaged by MHCII specific antibodies to any appreciable degree.

Not only hematopoietic cells of the immunological system but also cells of the epithelium (for instance insulin-producing cells of the Langerhans isles in the pancreas) and cells of the endothelium, especially in the degenerated state, or after stimulation express the MHCII-antigen in different forms. The proposed pharmaceutical compositions therefore also lend themselves to the immunotherapy of tumors deriving from such cells.

Apart from the use for tumor immunotherapy, the pharmaceutical compositions of the invention also lend themselves for instance to immunotherapy for attenuating or suppressing a host-versus-graft reaction. After an allogenic bone marrow transplantation, any residual MHCII positive cells of the receiver that have survived the patient's conditioning (for instance irradiation, chemotherapy) may lead to a graft rejection in the form of a host-versus-graft-reaction. Anti-MHCII antibodies (of the receiver's type) allow such immunocompetent cells of the receiver which prevent the "engraftment" (that is to say, taking, growing) of the new bone marrow or other donor organs, to be selectively attacked. The use of antibodies which apart from the receiver's MHCII-antigen recognize an antigen expressed on an immunocompetent MHCII positive cell, allows cells responsible for the rejection of the graft to be even more selectively eliminated.

Pharmaceutical compositions containing antibodies which specifically recognize activated T-cells, are for instance suitable to treat autoimmune reactions or lend themselves in general to selective immunosuppression.

The antibodies contained in the pharmaceutical compositions of the invention, may be antibodies possessing only one or more specificities. The term "specificity" as used herein means an antibody's capability of recognizing a particular antigen. The antigen can be recognized by one or more antigen binding sites of an antibody, and the binding sites are in turn able to recognize the same or different epitopes of the antigen.

In a preferred embodiment of the present invention the pharmaceutical compositions contain antibodies with one specificity only, which recognize the MHCII-antigen of a patient to be treated, that is to say the pharmaceutical compositions contain so-called monospecific antibodies. The use of such antibodies allows the elimination of MHCII-presenting cells, for instance by complement reactions or antibody-mediated cytotoxicity by means of Fc-receptor-carrying cells. The prerequisite therefor is that the antibodies that are used have an Fc-region.

Another preferred embodiment of the invention relates to pharmaceutical compositions containing antibodies with two or more specificities, one of which recognizes a patient's MHCII-antigen. In this case, one specificity recognizes the patient's MHCII-antigen, while another specificity may for instance recognize an antigen which is also present on the cell to be eliminated, or an antigen, which is localized on another cell, for-instance an effector cell, or any other antigen. In this connection, those antigens are to be named which enhance the effector function of the antibody, that is to say its ability to eliminate the antigen-carrying cell. They include for instance toxic substances as will be explained hereinbelow.

Antibodies having more than one specificity can be used in the pharmaceutical compositions of the invention for instance to increase the selectivity in the antibodies' recognition of a target cell to be eliminated, e.g. a tumor cell, compared to their recognition of other cells. As has already been explained above, some non-malign cells, for instance liver cells also present the MHCII-antigen on the cell surface, though in substantially smaller numbers. In order to increase the specificity for MHCII-expressing tumor cells of the antibodies that are used, it is for instance possible to employ antibodies which recognize two different antigens localized on the cell to be eliminated. These antibodies are so-called bispecific antibodies. Antibodies which recognize a tumor-associated antigen in addition to the MHCII-antigen of the patient to be treated are preferred.

In this connection, the term "tumor-associated" antigen means that such an antigen, compared to non-malign cells, will be preferably expressed by cells of the tumor to be treated, and/or occurs on non-malign cells in smaller numbers.

Moreover, the second antigen may be an antigen specifically expressed by the tissue from which the tumor derives.

Compared to monospecific antibodies which only recognize the MHCII-antigen or only recognize a tumor-associated or tissue-specific antigen, the bispecific antibodies have the advantage that they bind with substantially higher affinity and specificity to cells that present both antigens, than they bind to cells which present only one of the two antigens (Parham; Human Immunol. 12 (1985), 213; Wong and Colvin; J. Immunol. 139 (1987), 1369; see also FIG. 1).

In a particularly preferred embodiment of the pharmaceutical compositions of the invention, the antigen, which is recognized in addition to MHCII by an MHCII-specific antibody having two or more specificities, is an antigen which is expressed on leukemic cells, hematopoietic cells or degenerated cells of the endothelium or epithelium.

It is preferably the antigen CD1, CD2, CD3, CD4, CD5, CD6, CD7, CD8, CD10, CD11, CD11b, CD13, CD14, CD19, CD20, CD21, CD22, CD23, CD24, CD30, CD33, CD37, CD40, CD41, CD44v3, CD44v6, CD45R, CD56, CD71, B220, an Ig-idiotype, an IL-2-receptor, or an IL-6-receptor. Examples of antibodies suitable for the specific recognition of B-cell lymphomas are antibodies which recognize the antigens CD19, CD20, CD21, CD22, CD23, CD24, CD44v3, CD44v6, CD10, CD5, B220 or an Ig-idiotype, in addition to the MHCII-antigen. Antigens, such as CD1, CD2, CD3, CD4, CD5, CD6, CD7 and CD8 may be specifically assigned to T-cell lymphomas. The antigens CD11, CD13, CD14 and CD33 allow the specific recognition of myeloid leukemias, while the antigen CD41 allows the recognition of thrombocytic leukemias. By contrast, pharmaceutical compositions containing antibodies which recognize an IL-2-receptor in addition to the MHCII-antigen of the patient to be treated lend themselves to the specific recognition of cells of a Hodgkin lymphoma, an anaplastic "large cells" lymphoma or an adult T cell leukemia. Moreover, pharmaceutical compositions, where the antibodies recognize an IL-6-receptor apart from the MHCII-antigen of the patient to be treated lend themselves to the specific recognition of myelomas.

The elimination of cells, in particular tumor cells which are recognized by the herein-described antibodies contained in the pharmaceutical of the invention may occur in vivo by complement reactions or by antibody-mediated cytotoxicity by means of Fc-receptor carrying cells.

In another preferred embodiment, the pharmaceutical compositions according to the invention contain antibodies with two or more specificities, one specificity recognizing the MHCII-antigen of a patient to be treated and the other specificity recognizing the antigen which is specifically located on an effector cell. Such an antibody may have additional specificities as will be explained in the following.

The term "effector cell" means cells resulting from hematopoiesis and possessing cytolytical apoptosis-mediating or phagocytic properties. This term in particular comprises T-cells, granulocytes, monocytes, macrophages, NK (natural killer) cells, mast cells and Langerhans cells.

The antigen localized on the effector cell and recognized by the antibody is preferably the antigen CD1, CD2, CD3, CD4, CD5, CD8, CD11b, CD13, CD16, CD28, CD32, CD33, CD40L (also known as CD40 ligand), CD44, CD45R, CD56, CD64 or an interleukin-2-receptor.

Such antibodies allow effector cells to be activated and/or to be brought to the target cells, which results in the destruction of the latter.

Antibodies, which for instance recognize the antigen CD3 in addition to the MHCII-antigen of a patient to be treated are capable of activating T-cells and bringing them to the target cells (MHCII-expressing cells). This leads to the destruction of the target cells via T-cell-mediated mechanisms. Antibodies, which recognize the antigen CD28 that is also expressed on T-cells and serves the co-stimulation during stimulation by CD3, also allow effector cells to be activated. Similarly, antibodies which recognize the antigens CD16, CD32 or CD64, are able to activate Fc-receptor-positive cells, such as NK-cells granulocytes or macrophages and to bring them to the MHCII-carrying target cells, in particular tumor cells. This also leads subsequently to the destruction of the target cells.

Pharmaceutical compositions which contain antibodies recognizing the antigen CD3, CD16, CD28, CD32, or CD64, in addition to the patient's MHCII-antigen lend themselves not only to the above-described elimination of target cells in vivo but also to the in vitro application for eliminating tumor cells, particularly in allogenic bone marrow transplantation.

Antibodies which recognize the antigen combinations MHCII X CD1, MHCII X CD2, MHCII X CD4, MHCII X CD5, MHCII X CD6, MHCII X CD7, MHCII X CD8, MHCII X CD28, MHCII X CD40L, MHCII X CD45R or MHCII X interleukin-2-receptor, MHCII X interleukin-4-receptor, MHCII x interleukin-7-receptor, and in so doing especially recognize the antigen combinations MHCII x gamma-chain of the interleukin-2-receptor, the interleukin-4-receptor or interleukin-7-receptor are, moreover, suitable to recognize and eliminate activated T-cells, which may be important in connection with the suppression of a host-versus-graft-reaction, an autoimmuno-reaction or in eliciting a general immunosuppression.

Antibodies recognizing the antigen combinations MHCII X CD11b, MHCII X CD56 expressed on "natural killer" cells and antibodies recognizing the antigen combinations MHCII X CD13, MHCII X CD14 or MHCII X CD33 expressed on monocytes and macrophages are suitable for the same purpose.

In another preferred embodiment, the antibodies contained in the herein-described pharmaceutical compositions have one specificity, that is to say, they have one or more binding sites capable of specifically binding a toxic substance, for instance saporin or ricin. This allows the selective and direct elimination of the target cells by means of the toxin.

Moreover, according to another preferred embodiment of the pharmaceutical compositions of the invention, the antibodies contained in the pharmaceutical compositions are coupled to substances which enhance the effector function of the antibodies leading to the elimination of the target cell. Normally, the cell-destructive effect of antibodies stems from the effector functions of the Fc-region of the antibodies. For instance Fc-receptor-carrying cells can bind to a cell occupied by antibodies and can destroy it. This reaction, also called ADCC (antibody dependent cell mediated cytotoxicity), is often insufficient to effectively destroy all target cells.

The substances which can be coupled to the antibodies contained in the pharmaceutical compositions of the invention are preferably enzymes, toxic substances, biotin, radionuclides or superantigens.

In connection with the coupling of the antibody with an enzyme, for instance the so-called "antibody dependent enzyme mediated prodrug therapy" (ADEPT) described by Rodriguez et al (Cancer Res. 55 (1995), 63) should be mentioned. In this process, the prodrug of a toxic substance is activated directly at the envisaged site of activity, for instance at the tumor cells by an enzyme that is coupled to an antibody. This principle is the more efficient and free from side effects, the more specific the recognition of the target cells by the antibodies used. An enzyme preferably used in this method is for instance β-lactamase.

Examples of toxic substances which may be directly coupled to the antibodies used, are ricin, saporin or pertussis toxin.

The coupling of the antibody contained in the pharmaceutical to biotin, moreover, allows substances conjugated to avidin to accumulate at the target cells.

This is advantageous for instance in the application of radionuclide avidin conjugates. In this case, the conjugates are only administered when the antibody coupled to biotin is already bound to the target cell. Because of the high affinity between biotin and avidin, the conjugates accumulate with high specificity at the target cells. By contrast, unbound radionuclide-avidin conjugates are quickly removed from the organism on account of their small size. The advantage of using such antibodies in the pharmaceutical compositions of the invention is a relatively low unspecific radioactive irradiation of the patient. This advantage can be further enhanced by using antibodies with several specificities, which possess high target selectivity.

According to another preferred embodiment, the antibodies contained in the pharmaceutical compositions of the invention are coupled to a superantigen. Superantigens are extremely potent activators of T-cells. An example is the SEA ("staphylococcal enterotoxin A"). T-cells are induced by superantigens to proliferate and to release cytokines and to cytolyse adjacent cells. This uncontrolled, systemic T-cell activation is triggered by the superantigens' binding to conserved areas of MHCII-molecules or the Vβ chain of the T-cell receptors. Dohlsten et al. (Proc. Natl. Acad. Sci. USA 91 (1994), 8945) describes the possibility of replacing the unspecific binding at MHCII by a more specific antigen binding sites of an antibody. In this way, it is possible to have T-cell activation proceed in a substantially more controlled manner. The suitable combination of the antigen specificities of an antibody allows the cytolytic effect of activated T-cells to be limited to a particular target cell.

According to another preferred embodiment of the pharmaceutical compositions of the invention, the antibodies contained in the pharmaceutical compositions are present as antibodies on the membrane in so-called immunoliposomes. Immunoliposomes are liposomes which have antibodies bound on their surface (see for instance Phillips et al., J. Immunol. 152 (1994), 3168). The structure of a sterically stabilized immunoliposome is shown schematically in FIG. 2. Such liposomes may have cytotoxic agents incorporated in them. Antibodies which are located on membranes and specifically recognize a target cell, as described above, allow these liposomes to be purposively directed to the target cells. The high specificity mediated by the antibodies located on the membranes is very important because of the high toxicity of the agents included in the liposomes.

The antibodies contained in the above-described pharmaceutical compositions of the invention are preferably monoclonal, polyclonal, chimeric, recombinant, synthetic, semi-synthetic or chemically modified antibodies, and fragments of such antibodies, in particular Fv, Fab, scFv or F(ab)$_2$-fragments.

If the antibodies contained in the pharmaceutical compositions of the invention are intended for use in an in-vivo therapy, human antibodies or derivatives or fragments or antibodies, derivatives or fragments so modified that they lend themselves for use with humans are used (so-called "humanized antibodies") (see for instance Shalaby et al., J. Exp. Med. 175 (1992), 217; Mocikat et al., Transplantation 57 (1994), 405).

A skilled person is familiar with the preparation of the various above-mentioned antibody types and antibody fragments.

The preparation of monoclonal antibodies originating preferably from mammals, such as humans, rats, mice, rabbits or goats may be carried out by conventional methods, as described in Köhler and Milstein (Nature 256 (1975), 495), in Harlow and Lane (Antibodies, A Laboratory Manual (1988), Cold Spring Harbour) or in Galfré (Meth. Enzymol. 73 (1981), 3).

The preparation of polyclonal antibodies has likewise been described, for instance in Harlow and Lane (see above). Furthermore, it is possible to prepare the previously described antibodies by means of recombinant DNA technology according to techniques known to a skilled person (see for instance Kurucz et al., J. Immunol. 154 (1995), 4576; Holliger et al., Proc. Natl. Acad. Sci. USA 90 (1993), 6444).

The preparation of antibodies having two different specificities, the so-called bispecific antibodies can be carried out using recombinant DNA technology on the one hand, or the so-called hybrid-hybridoma fusion technique on the other hand (see for instance Milstein et al., Nature 305

(1983), 537). In this procedure, hybridoma cell lines which produce antibodies, each having one of the desired specificities, are produced and fused, and recombinants which produce antibodies having both specificities are identified and isolated.

The preparation of antibodies having three specificities, so-called trispecific antibodies, can for instance be carried out by coupling a third antigen binding site comprising another specificity, for instance in the form of a "single chain variable fragment" (scFv), to one of the heavy Ig-chains of a bispecific antibody. The scFv can be bound for instance via an

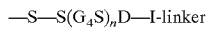

to one of the heavy chains (S=serine, G=glycine, D=aspartate, I=isoleucine). FIG. 6 schematically shows the structure of such a trispecific antibody which recognizes the antigen CD3 by means of the scFv-fragment coupled to it.

Trispecific F(ab)$_2$-constructs may be prepared analogously thereto, by replacing the CH2-CH3-regions of the heavy chain of one specificity of a bispecific antibody with an scFv having a third specificity, while the CH2—CH3 regions of the heavy chain of the different specificity are removed for instance by incorporation of a stop codon (at the end of the "hinge"-region) into the coding gene, for instance by homologous recombination (see FIG. 7).

The preparation of trispecific scFv-constructs is also possible. In this case, three VH-VL-regions representing three different specificities are arranged one after the other in a series (see FIG. 8).

In the preparation of antibodies which are coupled to a superantigen, for instance one of the heavy immunoglobulin chains of an antibody or antibody fragment is extended by a T-cell activating superantigen sequence. Said sequence may be connected for instance via an

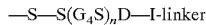

to one of the heavy Ig-chains. The addition of the linker and superantigen sequences to the heavy Ig-chain may for instance be brought about by homologous recombination on the DNA level in a hybridoma cell line (Lang and Mocikat, Mol. Gen. Genet. 242 (1994), 528). Such a construction of a bispecific antibody with a superantigen sequence is for instance shown in FIG. 3.

Moreover, it is possible to couple F(ab)$_2$ fragments to a superantigen. This is exemplified in FIG. 4 relative to a bispecific F(ab)$_2$fragment. In this case, the CH2, CH3 regions of a heavy immunoglobulin chain are replaced by a superantigen sequence, while the CH2 and CH3 regions of the other heavy immunoglobulin chain are removed by incorporation of a stop codon through homologous recombination.

Another possibility consists in coupling so-called "single chain variable fragments" (scFv) to a superantigen. This is exemplified in FIG. 5 relative to such a bispecific fragment. Only the V-regions having a different specificity are coupled in this procedure, while the constant antibody regions are completely removed, and subsequently a superantigen sequence is coupled to one of the V-regions, as described above.

The pharmaceutical compositions of the invention may contain, usual, pharmaceutically compatible carriers which are known to a skilled person, in addition to the afore-described antibodies.

A therapeutical scheme using a pharmaceutical according to the invention for eliminating residual tumor cells after an MHCII incompatible bone marrow transplantation can for instance consist in administering already at an early date after bone marrow transplantation antibodies specifically recognizing the receiver's MHCII-antigen and allowing the tumor cells to be eliminated by ADCC or complement mechanisms, or administering antibodies recognizing an antigen on an Fc-receptor-positive effector cell (for instance NK-cells, granulocytes or macrophages) in addition to the receiver's MHCII-antigen. As after a bone marrow transplantation, Fc-receptor-positive cells grow faster than T-cells from the donor bone marrow, it is possible to begin such a treatment as early as a few days after transplantation. When sufficient donor type T cells have been formed (this is the case when the T-cell portion in the peripheral blood exceeds 5%), it is possible to subsequently administer antibodies specifically recognizing not only the receiver MHCII-antigen but also the CD3 antigen. In consequence, the T-cells are activated and led to the MHCII expressing tumor cells, with the result that the latter are eliminated.

Such a combination of different therapeutical forms allows an effective and selective attack to be launched against these tumor cells already at an early stage when there are only a few surviving tumor cells in the patient and allows relative small amounts of antibodies to be used without any appreciable side effects. As the percentage of patients dying from leukemic recidivation after bone marrow transplantations continues to be very high (about 40%), such a mild therapeutical form involving few side effects can be used with all patient as a prophylactic measure without waiting for recidivation and the resulting lower chances of therapeutical success.

The pharmaceutical compositions of the invention lend themselves not only to the afore-described in vivo immunotherapy after MHCII-incompatible bone marrow transplantation but also to immunotherapy after autologous bone marrow transplantation and in general to in vivo and in vitro tumor depletion. By combining an anti-MHCII specificity with for instance an anti-CD10-specificity it is possible to so increase the selectivity for tumor cells of the antibodies contained in the pharmaceutical compositions that damages of other MHCII-carrying cells or tissues are almost totally excluded.

The present invention also relates to the antibodies contained in the pharmaceutical compositions according to the invention, monospecific antibodies recognizing one MHCII-antigen being excepted.

Hence, the present invention also relates to antibodies having two or ore specificities possessing at least one antigen binding site which specifically recognizes the MHCII-antigen of a patient to be treated. Moreover, the present invention relates to preferred embodiments of such antibodies as described above as components or active components of the pharmaceutical compositions of the invention.

Moreover, the invention relates to the use of such antibodies specifically recognizing the MHCII-antigen of a patient to be treated and its preferred embodiments, and the use of monospecific MHCII recognizing antibodies for preparing pharmaceutical compositions for the in vivo or in vitro immunotherapy, of in particular tumors, preferably leukemias and tumors from degenerated cells of the epithelium or endothelium. The use for preparing pharmaceutical compositions for treating B-cell lymphomas, Hodgkin lymphomas, anaplastic "large cell" lymphoma, adult T-cell leukemias or myelomas is of particular interest.

Moreover, the invention relates to the use of antibodies according to the invention, and monospecific antibodies recognizing a patient's MHCII-antigen, in order to suppress a host-versus-graft reaction, in order to suppress an autoimmune reaction or in order to elicit immunosuppression.

Another embodiment of the present invention relates to diagnostic compositions containing monospecific antibodies specifically recognizing the MHCII-antigen of a patient to be treated or containing the above-described antibodies of the invention.

FIG. 1 shows the principle of the mode of action of bispecific antibodies,

FIG. 2 is a schematic representation of the structure of so-called immunoliposomes, PC=phosphatidyl choline
PEG=polyethylene glycol
PE=phosphatidyl ethanolamine FIG. 3 is a schematic representation of a bispecific antibody coupled to a superantigen sequence
Sag=superantigen sequence
bsAk=bispecific antibody FIG. 4 is a schematic representation of a bispecific $F(ab)_2$-superantigen construct
Sag=superantigen sequence
$bsF(ab)_2$=bispecific $F(ab)_2$ fragment FIG. 5 is a schematic representation of a bispecific "single chain variable fragment" superantigen construct.
Sag=superantigen sequence
bs-scFv=bispecific "single chain variable fragment"

FIG. 6 shows a schematic representation of a trispecific antibody in which a "single chain variable fragment" recognizing CD3 has been coupled via a linker to one of the heavy chains of a bispecific antibody.
triAk=trispecific antibody FIG. 7 is a schematic representation of a trispecific $F(ab)_2$-construct, in which a heavy chain of a bispecific antibody has been replaced with an scFv-fragment which recognizes CD3, and in which the other heavy chain has been removed;

The example illustrates the invention.

EXAMPLE 1

In order to examine the utility of the MHCII-antigen as an operational, tumor-specific antigen permitting the specific elimination of MHCII-expressing tumor cells, Balb/c (I-$A^d$+)/C57BL/6 (I-$A^b$+) chimeric mice (MHCI- and MHCII-incompatible) were injected with $2 \times 10^4$ BCL1 cells (B cell lymphoma, I-$A^d$+).

Figure 1:
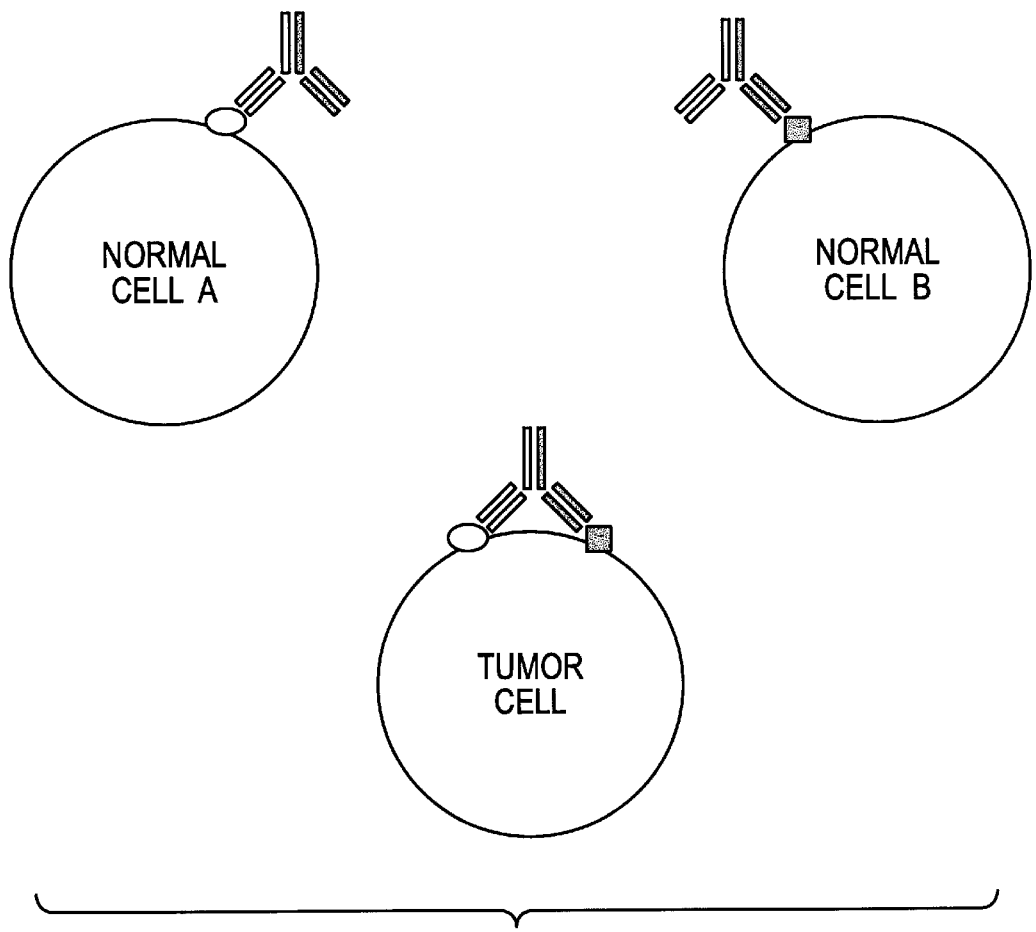
Figure 2:
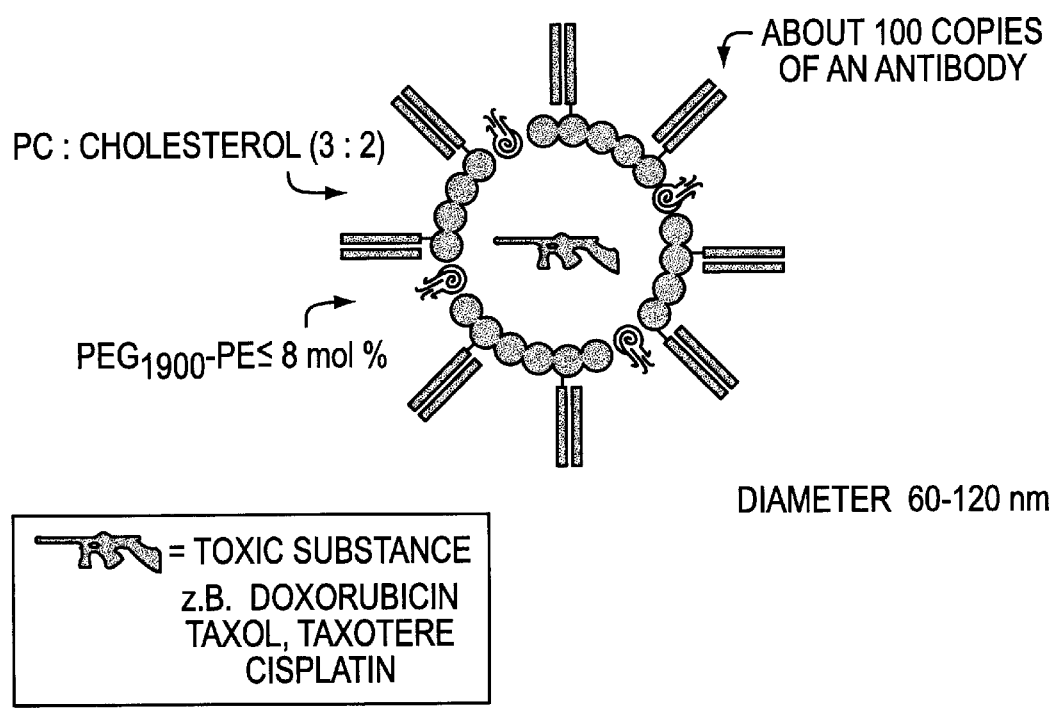
Figure 3:
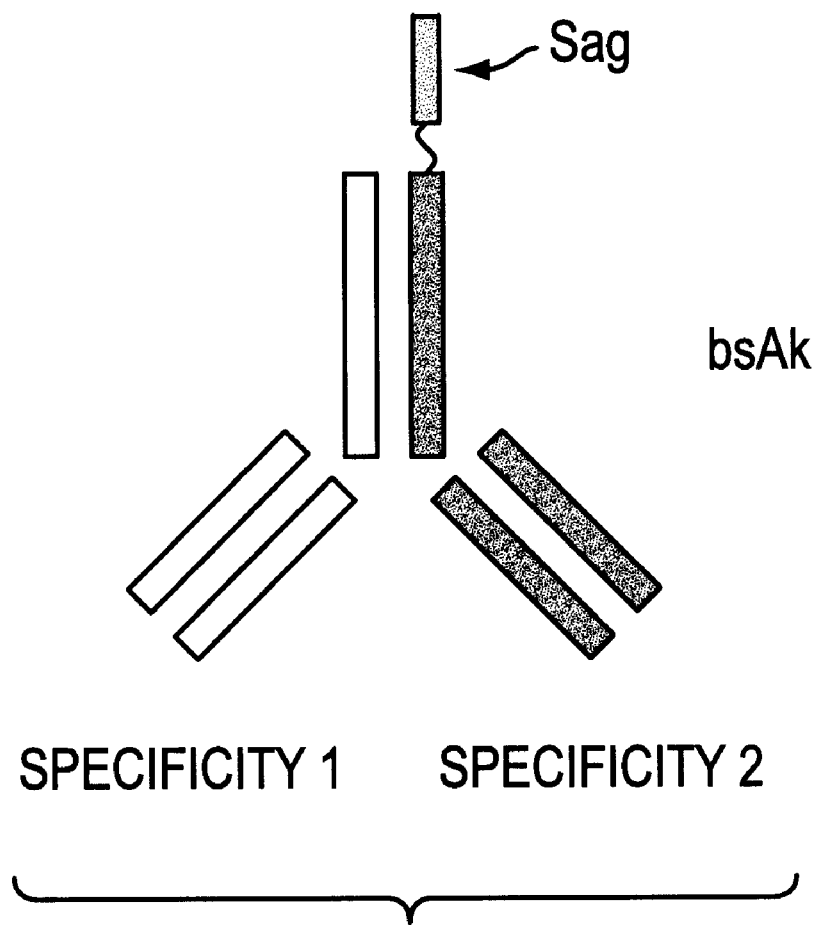
Figure 4:
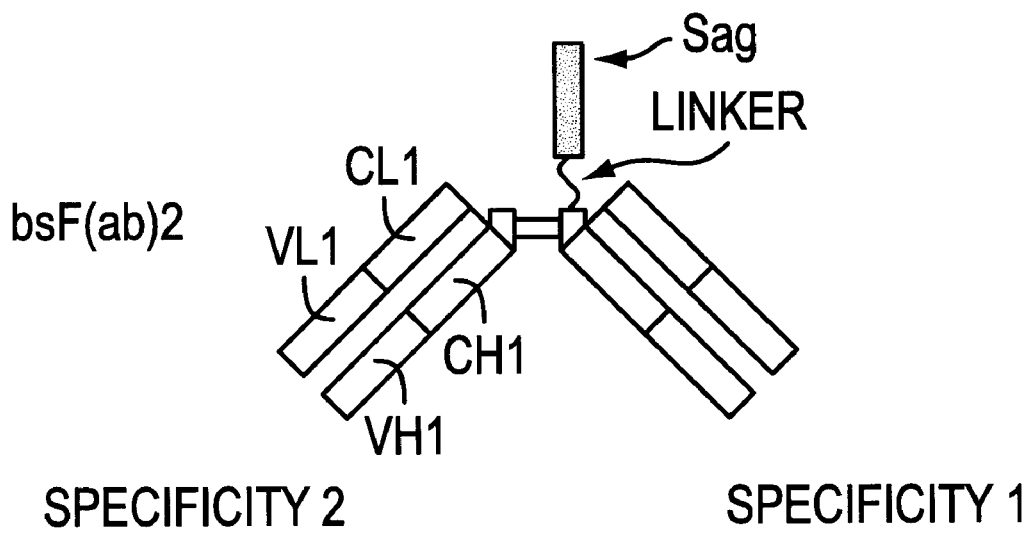
Figure 5:
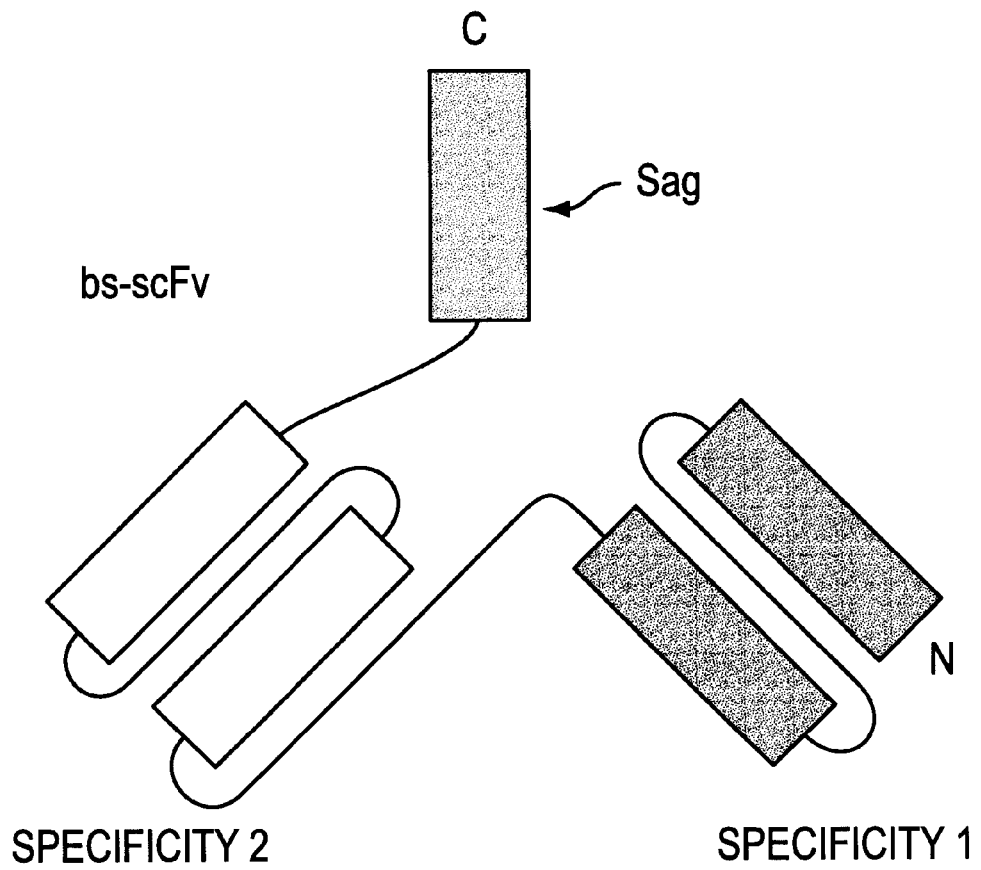
Figure 6:
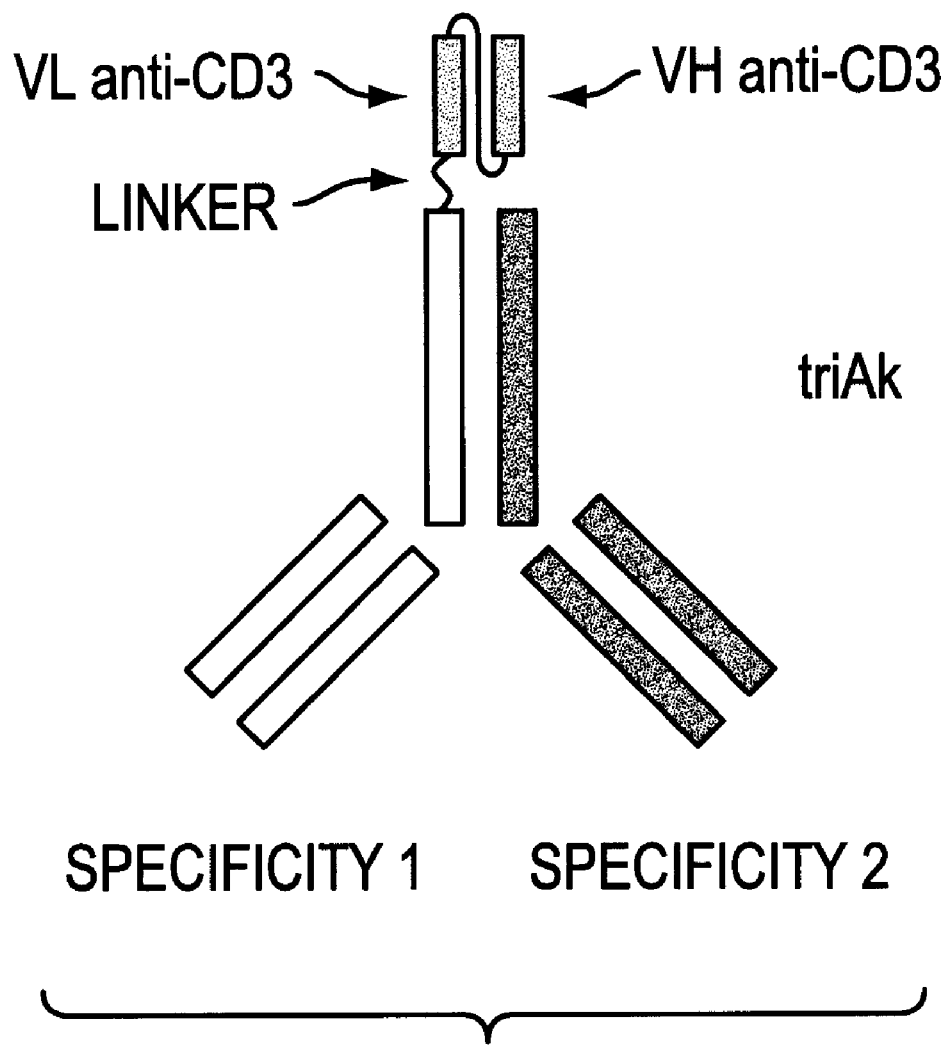
Figure 7:
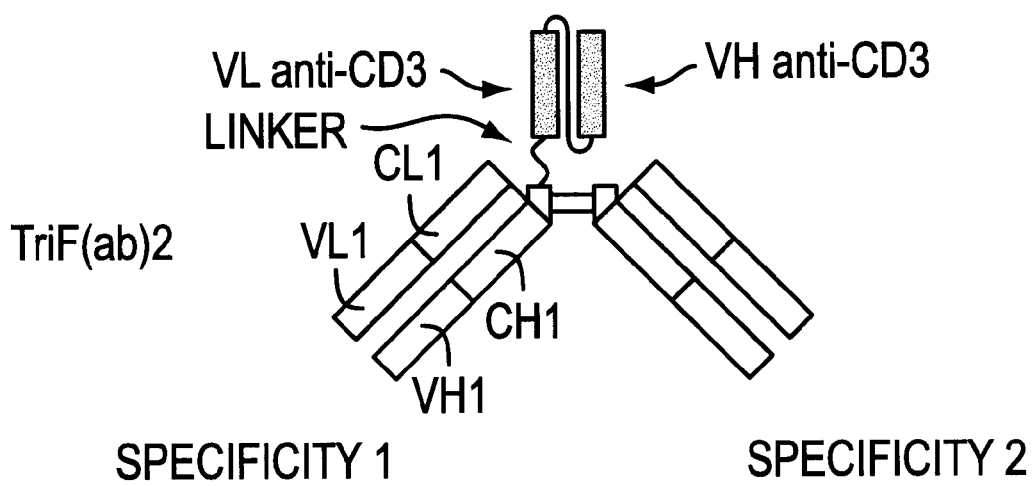
Figure 8:
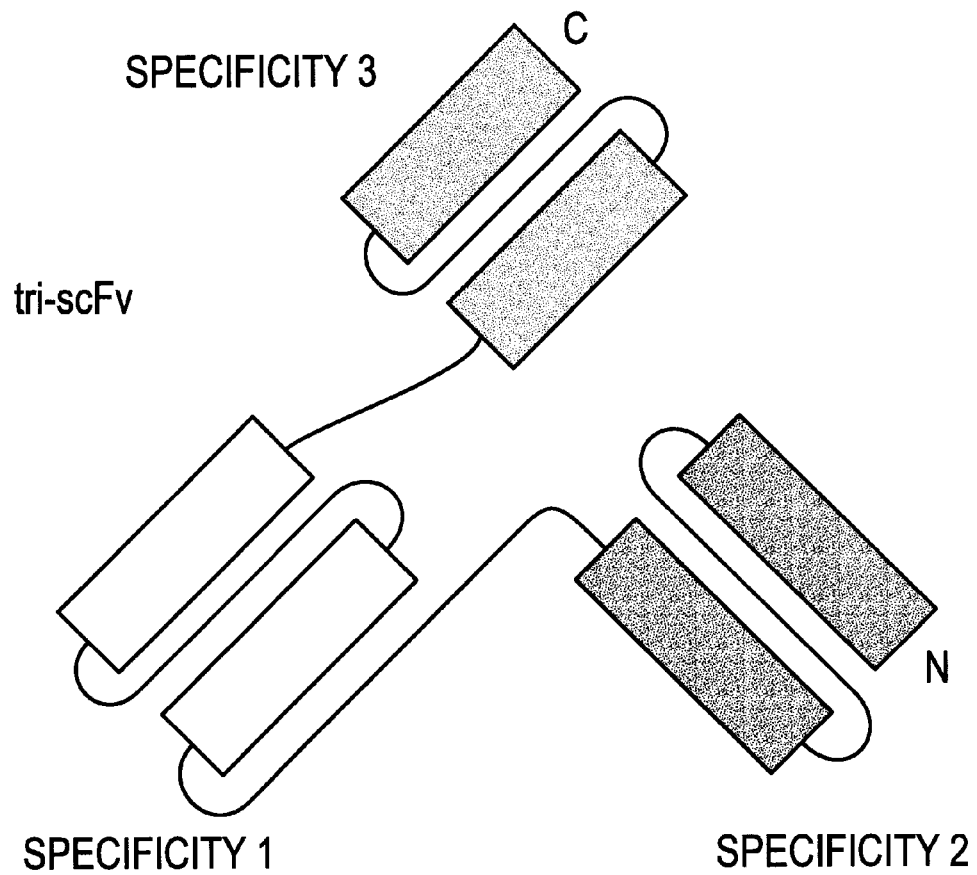
FIG. 8 is a schematic representation of a trispecific scFv-construct.
Figure 9:
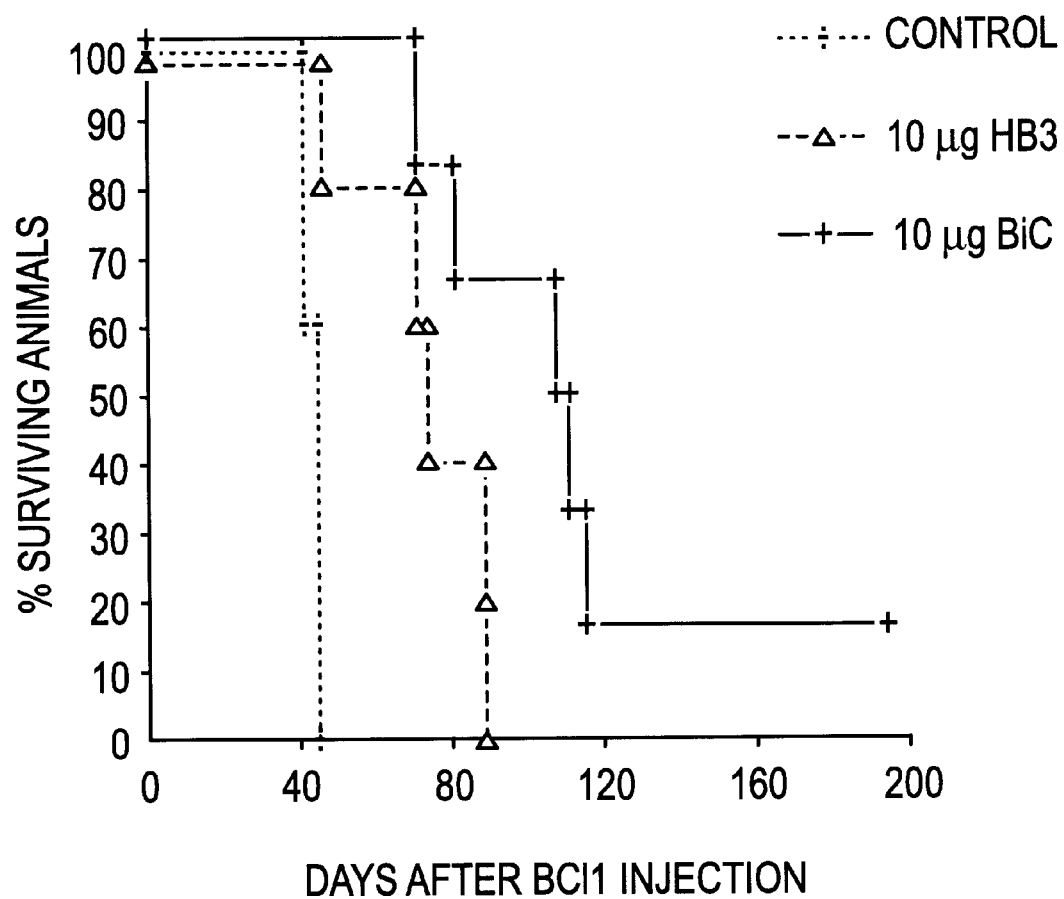
FIG. 9 shows the results of a test in which the Balb/c mice described in Example 1 are injected with BCL1-cells.
HB3=antibodies against MHCII-haplotype I-$A^d$
BiC=bispecific antibody with the specificities anti-I-$A^d$ and anti-CD3
As can be seen from this figure, a significant increase in the survival rate of mice injected with the MHCII-specific antibodies has been observed.

Four days later, the mice so treated were injected with 10 μg anti-I-$A^d$(MHCII) antibody. The mice thus treated showed a significant prolongation (log rank, p=0.04) of the survival time compared to the control mice that had been injected with $2 \times 10^4$ BCL1 tumor cells, but not with antibody (see FIG. 9).

What is claimed is:

1. A method for treating residual tumor cells in a mammalian subject comprising:

transplanting bone marrow cells from a donor to said subject wherein the immunocompetent cells of said donor transplanted to said subject are characterized by an MHCII-type antigen which differs from the MHCII type antigen expressed by said tumor cells; and administering to said subject a pharmaceutically effective amount of a composition comprising an antibody which selectively binds to MHCII antigen expressed by said tumor cells, whereby as a result of said selective binding, tumor cells carrying an antibody-MHCII antigen complex are destroyed.

2. The method of claim 1, wherein said antibody is a monospecific antibody.

3. The method of claim 1, wherein said antibody possesses one or more additional non-MHCII specificities.

4. The method of claim 1, wherein said antibody has an additional specificity which recognizes an antigen on an effector cell.

5. The method of claim 4, wherein the antigen of said effector cell is selected from the group consisting of CD1, CD2, CD3, CD4, CD5, CD6, CD7, CD8, CD11b, CD13, CD16, CD28, CD32, CD33, CD40L, CD45R, CD56, CD64 and an IL-2-receptor.

6. The method of claim 4, wherein the effector cell is selected from the group consisting of T-cells, granulocytes, monocytes, macrophages, NK (natural killer) cells, mast cells and Langerhans cells.

7. The method of claim 1, wherein said antibody further possesses a specificity for binding to a second antigen expressed on a cell type selected from the group consisting of leukemic cells, hematopoietic cells, malignant cells of the epithelium, and malignant cells of the endothelium.

8. The method of claim 7, wherein said second antigen is selected from the group consisting of CD1, CD2, CD3, CD4, CD5, CD6, CD7, CD8, CD10, CD11, CD11b, CD13, CD14, CD19, CD20, CD21, CD22, CD23, CD24, CD30, CD33, CD37, CD40, CD41, CD44v3, CD44v6, CD45R, CD56, CD71, B220, Ig-idiotype, an IL-2-receptor, an IL-6-receptor, and a tumor-associated antigen.

9. The method of claim 1, wherein said antibody is selected from the group consisting of monoclonal, recombinant, semisynthetic, chemically modified antibodies, and antigen binding fragments thereof.

10. The method of claim 10, wherein said antibody is coupled to a moiety selected from the group consisting of an enzyme, a toxic substance, a radionuclide, biotin and a superantigen.

11. The method of claim 10, wherein said tumor cells are leukemic cells.

12. The method of claim 11, wherein said leukemic cells are selected from the group consisting of B-cell lymphoma, Hodgkin-lymphoma, anaplastic "large cell" lymphoma, adult T-cell leukemia and myeloma cells.

13. The method of claim 1, wherein the tumor cells are malignant cells of the epithelium or endothelium.

* * * * *